United States Patent [19]

Nakamura

[11] Patent Number: 4,867,405
[45] Date of Patent: Sep. 19, 1989

[54] STAND MECHANISM FOR A MEDICAL OPTICAL EQUIPMENT

[75] Inventor: Katushige Nakamura, Tokyo, Japan

[73] Assignee: Mitaka Kohki Company Ltd., Mitaka, Japan

[21] Appl. No.: 195,753

[22] Filed: May 19, 1988

[51] Int. Cl.⁴ ............................................. E04G 3/00
[52] U.S. Cl. .............................. 248/281.1; 248/123.1; 248/280.1; 350/522
[58] Field of Search ............... 248/280.1, 281.1, 123.1, 248/325, 324, 585, 586, 587; 350/522, 321; 128/303.1; 74/103, 479, 105; 414/917, 1, 4

[56] References Cited

U.S. PATENT DOCUMENTS

| | | | |
|---|---|---|---|
| 3,475,075 | 10/1969 | Stone | 350/522 |
| 3,762,796 | 10/1973 | Heller | |
| 3,887,267 | 6/1975 | Heller | 350/522 |
| 3,891,301 | 6/1975 | Heller | 350/522 |
| 4,335,315 | 6/1982 | Waerve | 248/281.1 X |
| 4,339,100 | 7/1982 | Heller | 248/123.1 |
| 4,437,635 | 3/1984 | Pham | 414/917 |
| 4,453,883 | 6/1984 | Bisiach | 414/917 X |
| 4,551,058 | 11/1985 | Mosher | 414/917 |
| 4,668,057 | 5/1987 | Kleinberg | 350/522 X |
| 4,684,088 | 8/1987 | Heller | 414/917 X |
| 4,741,607 | 5/1988 | Heller | 350/522 |

Primary Examiner—J. Franklin Foss
Attorney, Agent, or Firm—Schwartz & Weinrieb

[57] ABSTRACT

A stand mechanism for medical optical equipment wherein the optical equipment is supported by a parallel linkage and the balance of weight with respect to all movement directions such as, for example, vertical, horizontal and pivotal directions of the parallel linkage is maintained. The optical equipment is disposed in a weight-balanced condition and therefore can be moved to any desired positon by means of small movement forces being exerted thereon and hence the movement operation can be carried out more exactly and more rapidly.

14 Claims, 5 Drawing Sheets

STAND MECHANISM FOR A MEDICAL OPTICAL EQUIPMENT

FIELD OF THE INVENTION

The present invention relates to a stand mechanism for supporting medical optical equipment.

BACKGROUND OF THE INVENTION

An encephalic surgical operation and a cardiac surgical operation are implemented by observing the diseased region with medical optical equipment, that is, for example, a surgical microscope, and such very delicate operations impose a high strain upon the nerves and, in most cases, requires a long time to perform, which undesirably causes both the surgeons and the support staff, as well as the patient physical and spiritual fatigue.

A medical optical equipment such as a surgical microscope plays a very significant role in advanced surgical operations, and the accessibility of the medical optical equipment has a direct effect upon reducing the time necessary for a surgical operation. The accessibility of the medical optical equipment, namely, the possibility of positioning the medical optical equipment accurately and quickly at an objective position corresponding to the diseased region to be operated upon, the possibility of moving the medical optical equipment away from the region of the operation to, and fixedly positioning the same at, an optional standby position and the stability of the medical optical equipment at a fixed position, is primarily dependent upon the performance of a stand mechanism supporting the medical optical equipment.

Various stand mechanisms for supporting medical optical equipment including stand mechanisms such as those disclosed in Japanese Patent Provisional Publication (Kokai) No. 56-32110 have been proposed. However, those known stand mechanisms are not sufficiently satisfactory with respect to the required accessibility during modern medical operations.

OBJECTS OF THE INVENTION

The present invention has been developed in view of those disadvantages of the prior art and it is therefore an object of the present invention to provide a stand mechanism for supporting medical optical equipment which is capable of properly functioning during medical operations and which is capable of enabling the medical optical equipment to properly perform all of the functions thereof.

BRIEF DESCRIPTION OF THE DRAWINGS

Various other features and advantages of the invention will be more apparent by referring to the following description and the accompanying drawings, wherein.

DESCRIPTION OF THE PREFERRED EMBODIMENTS

Figure 1:
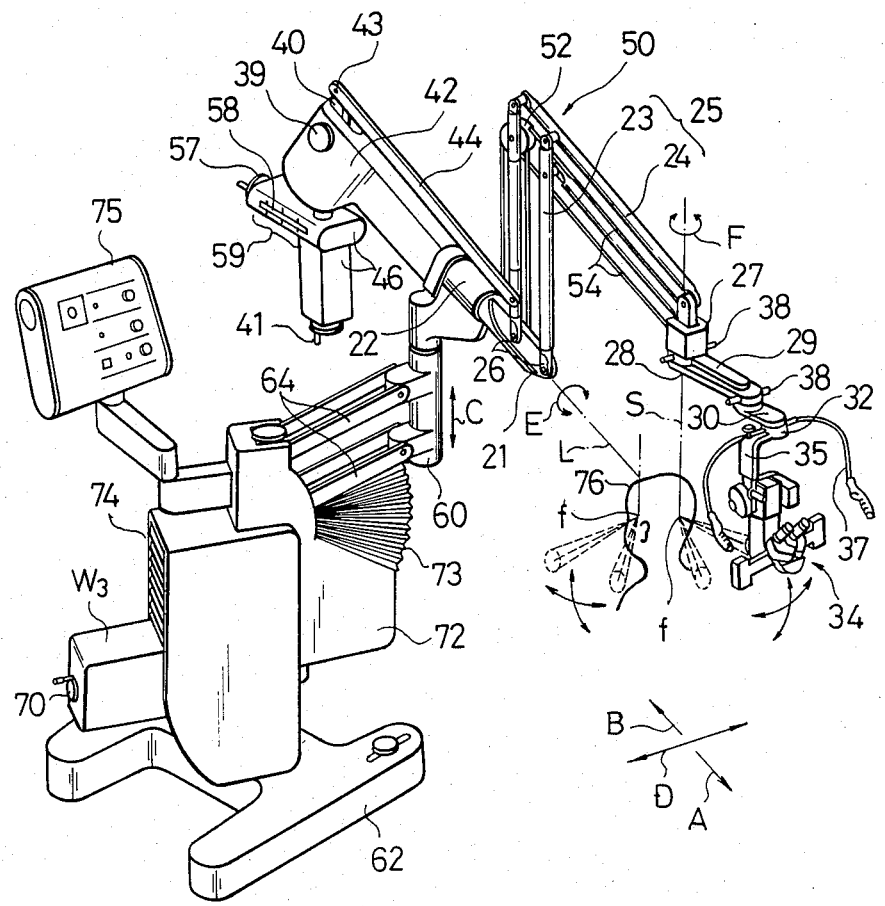
FIG. 1 is a general perspective view of a stand mechanism for medical optical equipment, embodying the present invention.
Figure 3:
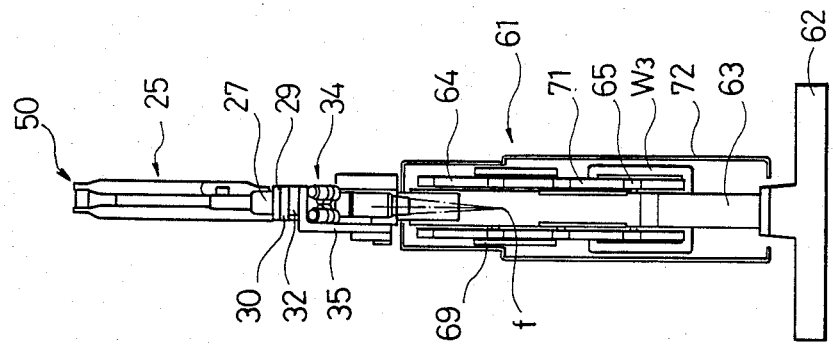
FIG. 3 is a schematic end elevational view as viewed in the direction of the arrow III in FIG. 2.

A stand mechanism for supporting medical optical equipment, in a preferred embodiment, according to the present invention will be described hereinafter with reference to the accompanying drawings.

First the constitution of the stand mechanism will be described, and then the operation of the stand mechanism will be described.

A central shaft 21 is rotatably supported within bearings housed within an inclined holding unit 22. The front end (that is, the end projecting in the direction indicated by the arrow A) of the central shaft 21 is machined so as to form a plate-shaped portion. Parallel links 23 and 24 of a parallel linkage system 25 are pivotably joined at the respective base ends 26 thereof to the plate-shaped portion of the central shaft 21.

Figure 8:
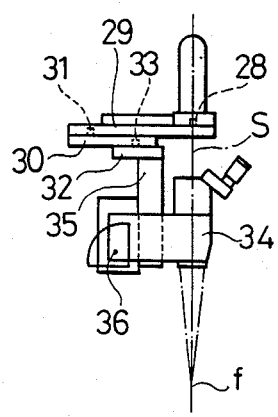
FIG. 8 is a side elevational view of the medical optical equipment disposed in a vertical orientation.

A swivel plate (swivel member) 29 serving as a supporting member is pivotably joined to the extremity 27 of the parallel linkage 25 for executing a turning motion about an axis of rotation 28 within a horizontal plane. A first swivel plate 30 is pivotably joined to the free end of the swivel plate 29 by means of a pivot shaft 31 for facilitating turning motion upon the pivot shaft 31 within a horizontal plane, as seen in FIG. 8. A second swivel plate 32 is pivotably joined to the free end of the first swivel plate 30 by means of a pivot shaft 33 for facilitating turning motion within a horizontal plane, also as seen in FIG. 8. A suspending arm 35 is supported by means of the second swivel plate 32, and a surgical microscope 34 (medical optical equipment) is pivotably supported upon the suspending arm 35 at a position directly below the second swivel plate 32 so as to be pivotable about a horizontal axis of rotation 36 between a vertical position, a 45°-inclined position where the surgical microscope 34 is inclined at an angle of 45° and a horizontal position where the surgical microscope is oriented within a horizontal plane. The focus f of the surgical microscope 34 is always located upon a vertical line S passing through the vertical axis of rotation 28 regardless of the position of the surgical microscope, which will be described in detail afterward. Moreover, since the focus f of the surgical microscope 34 is also positioned upon an extension L of a straight line connecting the base ends 26 of the parallel linkage 25 which are aligned with an extension of the central axis of central shaft 21, the position of the focus f remains unchanged when the parallel linkage is transformed. A handle 37 is provided for moving (swinging) the surgical microscope 34. Fixtures 38 are provided respectively at the base end and front end of the swivel plate 29 so as to change the position of the handle 37 according to the position of the operator.

Figure 2:
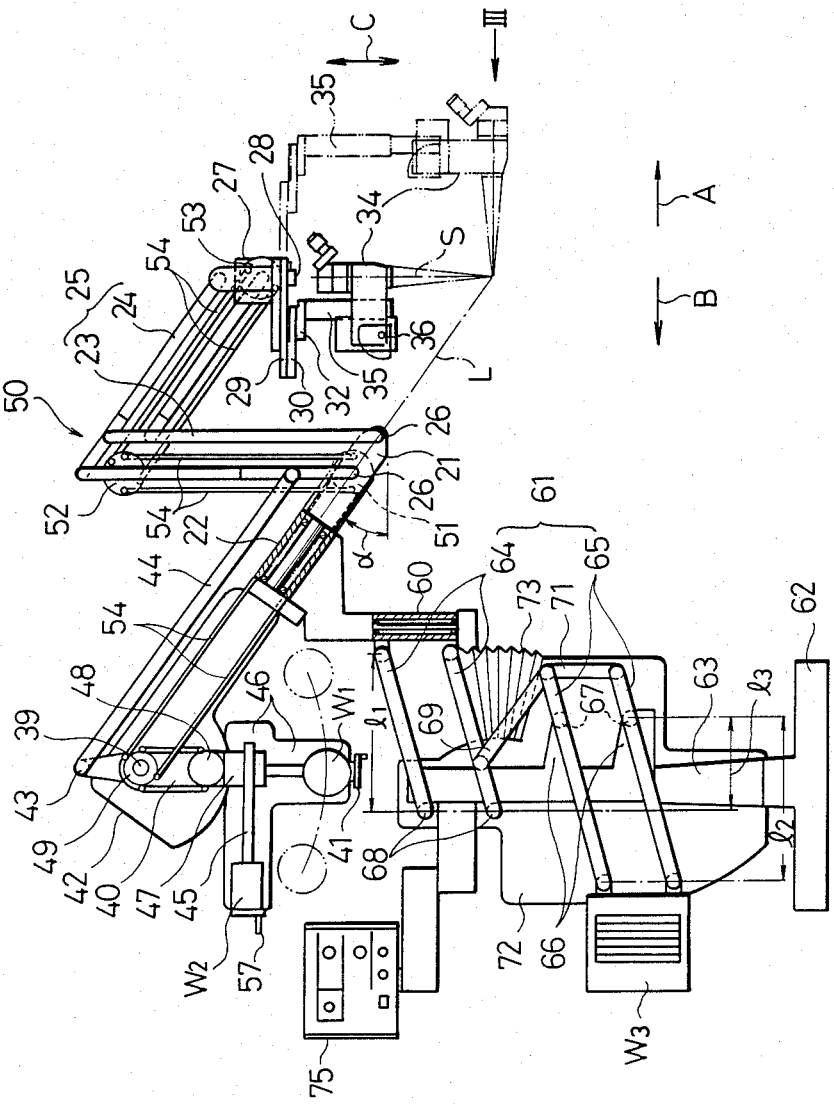
FIG. 2 is a schematic side elevational view showing the weight balancing system of the stand mechanism of FIG. 1.

A first pendulous counterweight W1 is suspended by means of a swing bar 40 from the rear end ( the end projecting in the direction indicated by means of the arrow B) of the central shaft 21, as best seen in FIG. 2, so as to be able to swing upon a pivot shaft 39. An adjusting handle 41 is associated with the first counterweight W1 so as to adjust the vertical position of the first counterweight W1. The root or base portion of the swing bar 40 is covered by means of a cover 42. The first counterweight W1 and a second counterweight W2 are covered by means of another cover 46.

The upper end 43 of the swing bar 40 and the parallel linkage 25 are interconnected by means of a connecting bar 44 so as to interlock the parallel linkage 25 and the first counterweight W1 together. Thus, the first counterweight W1 counterbalances the inclusive weight of the surgical microscope 34 and the parallel linkages 25, and the rotary moment of the parallel linkage 25 with respect to the central axis of the central shaft 21. Since the central shaft 21 is inclined at an angle $\alpha$ with respect to a horizontal line, the first counterweight W1 and its associated parts are excluded from the operating zone, so that a sufficiently wide and free operating zone can be secured for the surgeon.

Figure 5:
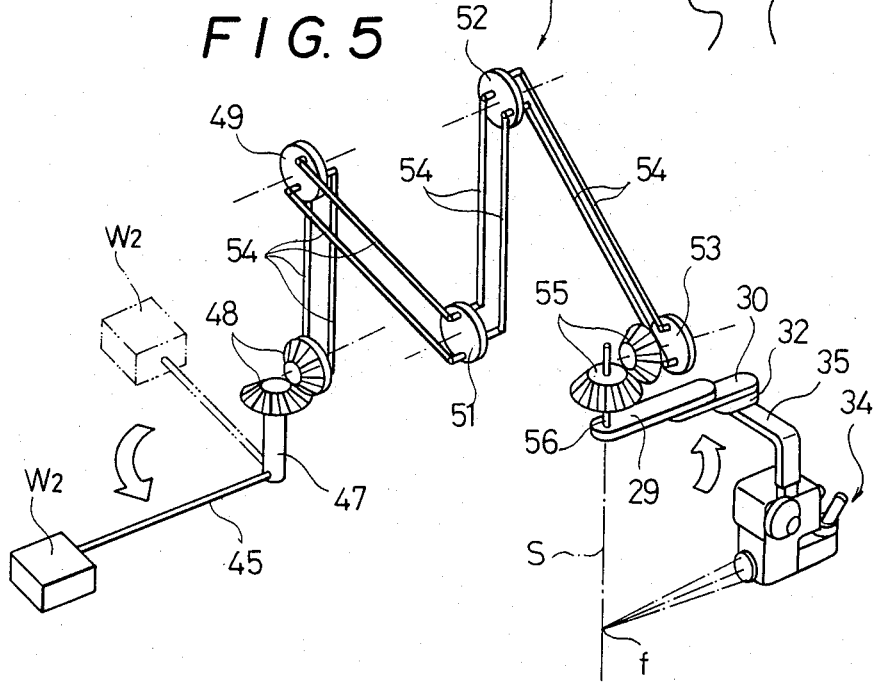
FIG. 5 is a fragmentary perspective view of a mechanism for swinging a counterweight according to the turning motion of a swivel plate within a horizontal plane.

The second counterweight W2 is connected by means of another swing bar 45 to the middle of the swing bar 40 suspendingly supporting the first counterweight W1. The second counterweight W2 is able to swing within a vertical plane together with the first counterweight W1 and is able to be swung within a horizontal plane by means of a mechanism which will be described afterward. That is, the base end of the swing bar 45 for the second counterweight W2 is fixed to a pivot shaft 47 which is coaxial with the swing bar 40, and the second counterweight W2 moves along a semicircular path with respect to the pivot shaft 47 as seen, for example, in FIG. 5. The pivot shaft 47 is interlocked with a rotary disk 49 provided near the rear end of the central shaft 21 through means of a pair of bevel gears 48 respectively having axes of rotation perpendicular to each other as heat seen in FIG. 5. Disks pivotable disks 51, 52 and 53, which are similarto the disk 49, are respectively provided near the base ends 26 of the parallel linkage 25, the articulated portion 50 of the parallel linkage 25 as may best be seen from FIGS. 2 and 5 and the extremity 27 of the parallel linkage 25. One of the bevel gears 48 and the disks 49, 51, 52 and 53 are interlocked by means of a plurality of pairs of link bars 54 so as to transmit torque therethrough. The disk 53 provided near the extremity 27 of the parallel linkage 25 is interlocked with the swivel plate 29 by means of a pair of bevel gears 55. One of the bevel gears 55 is fixed to the disk 53 and the other bevel gear 55 is fixed to a pivot shaft 56 which is, in turn, fixed to the swivel plate 29 and engages the former bevel gear 55. Accordingly, when the swivel plate 29 is pivoted within a horizontal plane, the turning motion of the swivel plate 29 is transmitted through the pivot shaft 56, the bevel gears 55, the disk 53, the disk 52, the disk 51, the disk 49, the bevel gears 48 and the pivot shaft 47 in that order to the swing bar 45 supporting the second counterweight W2 so as to pivot the swing bar 45 within a horizontal plane in a direction which is the same as that of the pivotable motion of the swivel plate 29, so that the swivel plate 29 and the swing bar 45 supporting the second counterweight W2 extend respectively in opposite directions. Thus, the rotary moment with respect to the central shaft 21 produced by means of the pivotable motion of the swivel plate 29 is counterbalanced. The position of the second counterweight W2 upon the swing bar 45 can also be adjusted according to the inclination (0°,45° or 90°) of the surgical microscope 34 by rotating an adjusting handle 57 shown in FIGS. 1 and 2. A slit 58 is formed within a portion of the cover 46 covering the second counterweight W2. Three notches 59 are formed in association with the slit 58 at positions corresponding respectively to the three inclinations of the surgical microscope 34. The position of the second counterweight W2 upon the swing bar 45 can easily and accurately be adjusted according to the inclination of the surgical microscope 34 by turning the adjusting handle 57 so as to bring a countermark upon the second counterweight W2 into alignment with one of the notches 59 corresponding to the inclination of the surgical microscope 34.

The holding unit 22 pivotably supporting the central shaft 21 has a lower cylindrical part 60 rotatably supported in bearings. The cylindrical part 60 is joined to links of a multiple parallel linkage 61 as seen in FIG. 2. Thus, the multiple parallel linkage 61 supports the holding unit 22 and the cylindrical part 60. The multiple parallel linkage 61 supports the inclusive weight of the central shaft 21 and all the components supported upon the central shaft 21 for vertical movement. The multiple parallel linkage 61 is pivotably supported upon an upstanding swivel stand shaft 63 for providing swivel motion upon a base 62. The multiple parallel linkage 61 has two pairs of upper parallel links 64 and two pairs of lower parallel links 65 disposed parallel to each other. The lower parallel links 65 are respectively pivotably supported upon pivot shafts 67 attached respectively to the extremities of projections 66 projecting from the stand shaft 63. The upper parallel links 64 are pivotably supported, respectively, above the lower parallel links 65 upon pivot shafts 68 provided near the upper end of the stand shaft 63. The upper parallel links 64 and the lower parallel links 65 are interlocked with each other by means of connecting links 69. A third counterweight W3 for counterbalancing the inclusive weight of the central shaft 21 and the components supported upon the central shaft 21 (hereinafter referred to as the "upper structure") is joined to the rear ends of the lower parallel links 65. The position of the third counterweight W3 can be adjusted by means of an adjusting handle 70 shown in FIG. 1. If a single parallel linkage is used instead of the upper parallel linkage essentially consisting of the upper parallel links 64 having an effective length $l_1$ (that is, the distance defined betwen the holding unit 22 and the pivot shafts) and the lower parallel linkage essentially consisting of the lower parallel links 65 having an effective length $l_2$ (that is, the distance defined between the pivot shafts 67 and the third counterweight W3) so as to support the upper structure, the effective length of the links of the single parallel linkage is the sum of the effective lengths $l_1$ and $l_2$. However, the use of the upper parallel links 64 and the lower parallel links 65 permits the size of the stand mechanism to be determined by the horizontal distance $l_3$ defined between the pivot shafts 67 and the pivot shafts 68, which enables the stand mechanism to be formed in so as to have a compact construction. Furthermore, since the rearward projection of the third counterweight W3 is small, the third counterweight W3 will not interfere with the peripheral equipment, which is advantageous from the viewpoint of securing safety. Connecting links 71 are provided so as to reinforce the lower parallel links 65. The stand shaft 63 and the lower parallel links 65 are covered by means of a cover 72. Openings in within the cover 72 for accommodating the vertical movement of the upper parallel links 64 and the third counterweight W3 are covered by means of bellows covers 73 and 74, respectively. Indicated at 75 is a control panel. The stand mechanism has electromagnetic clutches, not shown, respectively provided at the articulated portions and are selectively operated by means of a foot switch or the like so as to selectively lock or free the components.

The operation of the stand mechanism will now be described hereinafter.

Longitudinal Motion (Directions A and B)

Figure 6:
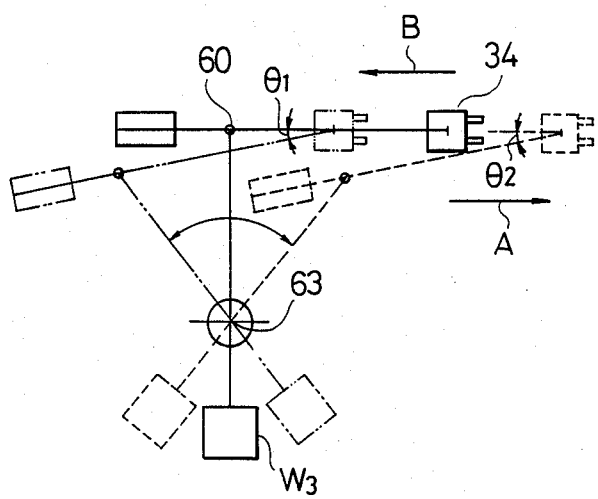
FIG. 6 is a schematic plan view for assisting in explaining the motion of the stand mechanism of FIG. 1 during movement of the medical optical equipment in longitudinal directions.

As shown in FIG. 6, when the surgical microscope is moved in a longitudinal direction, the stand shaft 63 and the cylindrical part 60 are pivoted accordingly. An angle $\theta_1$ or $\theta_2$ of deviation of the surgical microscope 34 with respect to the parallel linkage 25 due to the movement of the surgical microscope 34 in the direction of the arrow B or A is automatically compensated for as a result of the pivoting of the swivel plate 29 supporting the surgical microscope 34 in one of the directions indicated by the double-head arrow F as shown in FIG. 1, and hence the surgical microscope 34 can be translated in longitudinal directions without varying the observation angle thereof.

Vertical Motion (Directions C)

When the surgical microscope 34 is moved in a vertical direction, the multiple parallel linkage 61 is transformed and the upper structure is moved in the same direction. Since the moment of the upper structure is counterbalanced by that of the third counterweight W3, the upper structure can easily be moved in an effortless manner in vertical directions.

Lateral Motion (Directions D)

Figure 7:
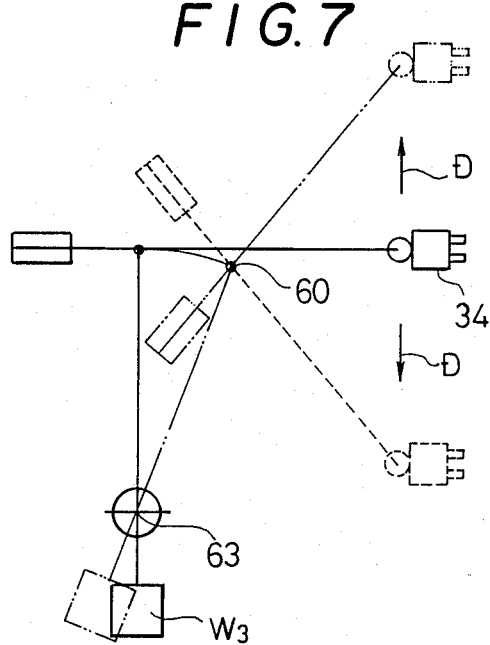
FIG. 7 is a schematic plan view for assisting in explaining the motion of the stand mechanism of FIG. 1 during movement of the medical optical equipment in lateral directions.

As shown in FIG. 7, when the surgical microscope 34 is moved in a lateral direction, the stand shaft 63 and the cylindrical part 60 pivot accordingly. Since the angle of deviation of the surgical microscope 34 with respect to the parallel linkage 25 attributable to the longitudinal movement of the surgical microscope 34 is automatically compensated for as a result of the pivoting of the swivel plate 29 supporting the surgical microscope 34 in one of the directions of the double-head arrow F, the surgical microscope 34 can be translated in lateral directions without varying the observation angle thereof.

Figure 4:
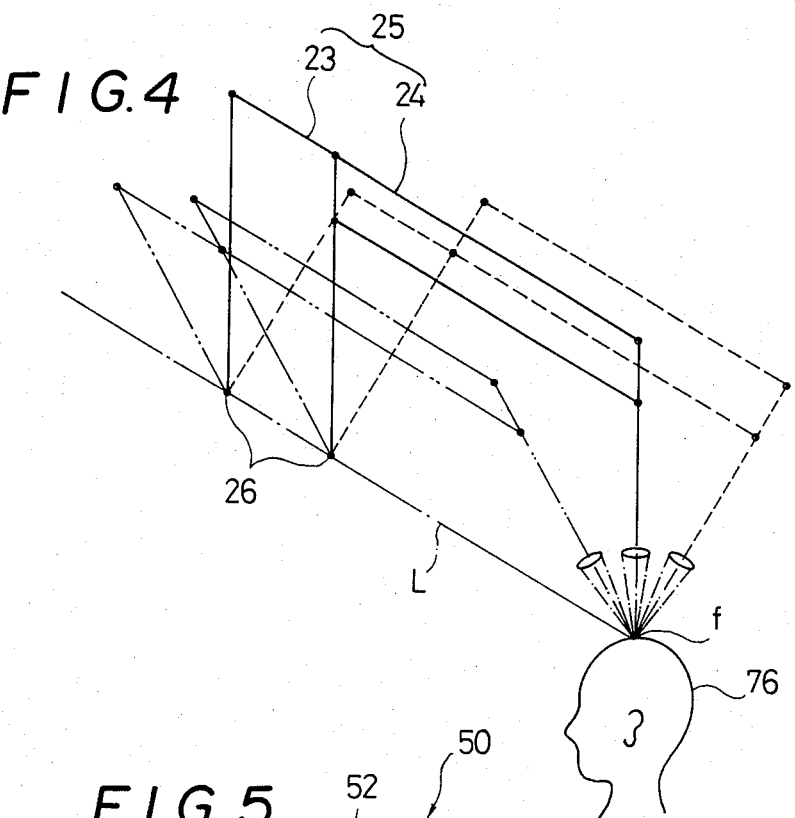
FIG. 4 is a diagrammatic illustration for assisting in explaining the operation of a parallel linkage for adjusting the observation angle of the medical optical equipment within a plane including the parallel linkage.

Adjustment of Inclination of Surgical Microscope (FIG. 4)

Since the focus f of the surgical microscope 34 is located upon the extension L of the straight line connecting the base ends 26 of the parallel linkage 25, namely, upon the extension of the central axis of the central shaft 21, the focus f remains fixed at the original position when the parallel linkage 25 is transformed. Accordingly, the observation angle can optionally be adjusted within a plane including the parallel linkage 25. When the parallel linkage 25 is transformed, both the first counterweight W1 and the second counterweight W2 are caused to pivot. Therefore, the inclusive weight of the surgical microscope 34 and the parallel linkage 25 is counterbalanced by means of the first counterweight W1 and the second counterweight W2 so as to automatically maintain balanced stability. The position of the first counterweight W1 upon the swing bar 45 must be adjusted by means of the adjusting handle 41 according to the weight of any accessories, such as, for example, a microscope for the assistant and a video camera, which are additionally mounted upon the surgical microscope 34.

Turning Motion of Central Shaft (Directions E)

When the surgical microscope 34 is pivoted about the central axis of the central shaft 21, the parallel linkage 25 is likewise pivoted about the central axis of the central shaft 21 in the same direction, and hence the first counterweight W1 and the second counterweight W2 are swung in the same direction together with the swing bar 40. Accordingly, the balance of weight is maintained and hence the surgical microscope 34 is positioned at an optional stationary position.

Horizontal Pivoting of the Swivel Plate (Directions F)

Since the swivel plate 29 is capable of undergoing swivel motion within a horizontal plane, the surgical microscope 34 can be moved around the head 76 of the patient in directions denotes by means of the double-head arrow F. When the swivel plate 29 deviates from a position which is an the extension of parallel linkage 25, for example, when the swivel plate 29 is pivoted to a position where the swivel plate 29 extends perpendicularly to the extension of the parallel linkage 25, the swing bar 45 supporting the second counterweight W2 is pivoted through means of the disks 49, 51, 52 and 53, the link bars 54 and the bevel gears 48 and 55 to a position where the swing bar 45 extends in the opposite direction with respect to the swivel plate 29. Accordingly, the balance of weight is maintained and hence the surgical microscope 34 will not automatically pivot any further about the central axis of the center shaft 21 in the directions of the double-head arrow E.

Furthermore, since the inclination of the swing bar 40 supporting the second counterweight W2 is always the same as that of the surgical microscope 34 due to the functions of the parallel linkage 25 and the connecting arm 44, the second counterweight W2 functions perfectly in maintaining the balance of weight regardless of the position of the swivel plate 29, and hence the balance of weight with respect to the pivotal directions of the central shaft 21 is never destroyed.

Still further, since the second counterweight W2 swings about the pivot shaft 47 without varying the center of gravity of the upper structure, the counterbalancing function of the third counterweight W3 is constantly maintained.

Changing The Observation Angle by Tilting the Surgical Microscope

In some cases, the observation angle of the surgical microscope 34 needs to be changed thrugh means of a large angle depending upon the position of the operative field. For example, an encephalic surgical operation includes operation upon the parietal region of the head 76 and operation upon the temporal region of the head 76. The present invention stand mechanism is provided with the first swivel plate 30 and the second swivel plate 32 so as to enable a change in the observation angle through a wide angular range.

Vertical Position:

Both the first swivel plate 30 and the second swivel plate 32 are pivoted toward folded positions below the swivel plate 29 so as to extend toward the axis of rotation 28 of the swivel plate 29 as shown in FIG. 8.

Figure 9A:
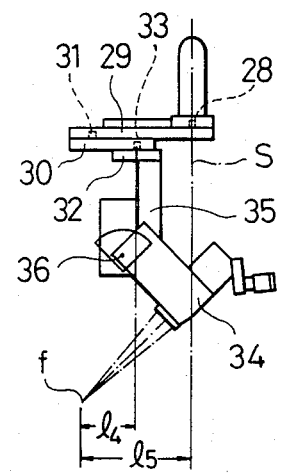
FIGS. 9(a) to 9(c) are side elevational views showing the process of changing the position of the medical optical equipment from a vertical position to a 45°-inclined position.
Figure 9B:
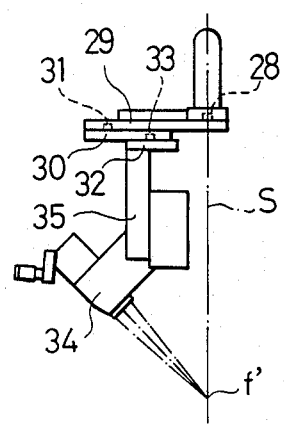
Figure 9C:
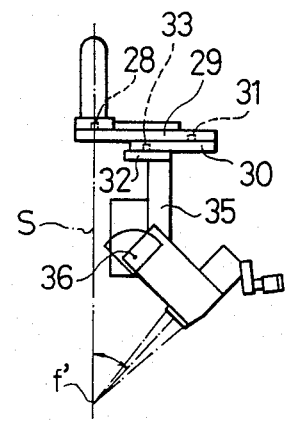

45°-Inclined Position:

First, the surgical microscope 34 is tilted from the vertical position through means of an angle of 45° about the axis of rotation 36 (FIG. 9(a)). In this state, the focus f is located upon a vertical line at a distance $l_5$ from the vertical line S upon which the focus f is located when the surgical microscope 34 is in a vertical position and at a distance $l_4$ from the central axis of the pivot shaft 33. The distance $l_5$ is exactly twice the distance $l_4$. Accordingly, when the second swivel plate 32 is pivoted through means of an angle of 180° upon the pivot shaft 33, the focus f' is located upon the vertical line S (FIG. 9(b)). Then, when the swivel plate 29 is pioted through means of an angle of 180° about the axis of rotation 28, the focus f' remains upon the vertical line S whereby the operator is able to observe the operative field though means of the surgical microscope 34 from th same general position as that of FIG. 9(a), notwithstanding the fact that the surgical microscope 34 is tilted at an inclination of 45° (FIG. 9(c)). Accordingly, the focus f' can be brought to the original position of the focus f by moving the surgical microscope 34 in the vertical direction by means of a lifting mechanism, not shown, incorporated within the surgical microscope 34.

Figure 10A:
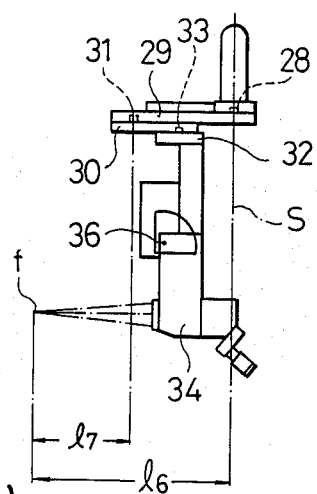
FIGS. 10(a) to 10(c) are side elevational views showing the process of changing the position of the medical optical equipment from a vertical orientation to a horizontal orientation.
Figure 10B:
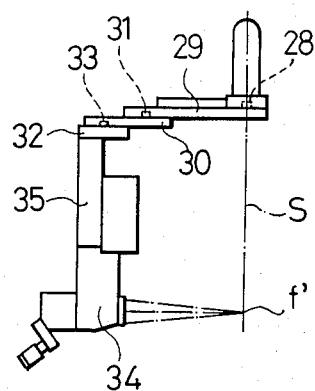
Figure 10C:
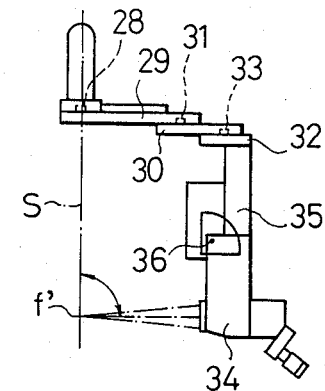

Horizontal Position:

The surgical microscope 34 which is disposed in a vertical position is pivoted through means of an angle of 90° about the axis of rotation 36 (FIG. 10(a)). In this state, the focus f is located upon a vertical line at a distance $l_6$ from the vertical line S and at a distance $l_7$ from the central axis of the pivot shaft 31. The distance $l_6$ is exactly twice the distance $l_7$. Accordingly, the focus f' can be located upon the vertical line S by pivoting the first swivel plate 30 through means of an angle of 180° upon the pivot shaft 31 (FIG. 10(b)). Then, when the swivel plate 29 is pivoted through means of an angle of 180° about the axis of rotation 28, similar to the case of the 45°-inclined position, the focus f' remains upon the vertical line S and the operator is able to observe the operative field through means of the surgical microscope 34 from the same position as that of FIG. 10(a), notwithstanding the fact that the surgical microscope 34 is disposed at a horizontal orientation (FIG. 10(c)).

Although the multiple parallel linkage 61 of the stand mechanism in this embodiment is a two-unit parallel linkage, the multiple parallel linkage may be a three-unit parallel linkage or a multiple parallel linkage having more than three units. Furthermore, although the invention has been described as applied to supporting a surgical microscope as an exemplary type of medical optical equipment, the present invention is applicable to supporting various types of medical equipment such as, for example, medical laser equipment. Still further, although the stand mechanism in this embodiment is a floor type stand mechanism, the present invention is also applicable to a suspension type stand mechanism for the same function.

The stand mechanism for medical optical equipment, according to the present invention provides the following effects:

(a) Since the inclusive weight of the optical equipment and the parallel linkage, as well as the rotary moment of the parallel linkage with respect to the central axis of the central shaft are counterbalanced by means of the pendulous counterweights, the stand mechanism embodies a simple construction and is able to operate smoothly in a satisfactory balance of weight condition without generating noises and squeaks. The employment of the pivotable central shaft eliminates the need for a counterweight for balancing the weight of the parallel linkage with respect to the pivotal direction and simplifies the construction of the stand mechanism.

(b) Since the rotary moment with respect to the axis of the central shaft resulting from the pivotal motion of the supporting unit is counterbalanced by means of the counterweight, the balance of weight about the central shaft is maintained when the supporting unit supporting the heavy medical optical equipment is pivoted within a horizontal plane and therefore the pivotal movement of the medical optical equipment can be stopped at any desired position.

(c) Since the holding unit is supported for vertical movement upon the extremity of the uppermost parallel linkage of the multiple parallel linkage, and the counterweight for counterbalancing the weight of the holding unit is provided upon the rear end of the lowermost parallel linkage of the multiple parallel linkage of the multiple parallel linkage, the upper structure can be easily moved vertically. Moreover, the stand mechanism has a pleasing appearance and, since the counterweight does not project rearwardly, the counterweight will not interfere with the operator and the peripheral equipment, which is advantageous from the viewpoint of safety.

(d) Since the focus of the optical equipment in the 45°-inclined positioned or at the horizontal position can be located at a position where the focus is located when the optical equipment is at the vertical position by pivoting the first swivel plate or the second swivel plate through means of an angle of 180° within a horizontal plane, the medical optical equipment can be used at an optimum observation angle. Moreover, sinc the focus moves along the same vertical line, the medical optical equipment can be focused remarkably quickly thereby reducing the time necessary for a surgical operation.

Obviously, many modifications and variations of the present invention are possible in light of the above teachings. It is therefore to be understood that within the scope of the appended claims, the present invention may be practiced otherwise than as specifically described herein.

What is claimed is:

1. A stand mechanism for supporting medical optical equipment, comprising:

parallel linkage means for supporting said optical equipment upon one extremity end thereof;

rotary shaft means, rotatable about a longitudinal axis thereof and having one end thereof connected to a second extremity end of said parallel linkage means such that said parallel linkage means extends substantially radially outwardly from said longitudinal axis of said rotary shaft means in a first direction with respect to said longitudinal axis of said rotary shaft means, for supporting said parallel linkage means and said optical equipment; and counterweight means, movably mounted upon an opposite end of said rotary shaft means and extending substantially radially outwardly from said longitudinal axis of said rotary shaft means in a second direction opposite to said first direction of said parallel linkage means with respect to said longitudinal axis of said rotary shaft means, for counterbalancing the weight of said optical equipment and said parallel linkage means, and the moments created thereby, with respect to said longitudinal axis of said rotary shaft means when said parallel linkage means is transformed substantially within a plane which includes said parallel linkage means and said longitudinal axis of said rotary shaft means as a result of positional movement of said optical equipment, and when said optical equipment and said parallel linkage means are pivotably moved about said longitudinal axis of said rotary shaft means.

2. A stand mechanism as set forth in claim 1, further comprising:

means defined upon said one extremity end of said parallel linkage means supporting said optical equipment for defining a vertical axis about which said optical equipment can be pivotably adjusted within a horizontal plane and upon which said optical equipment can be focused;

a first swivel plate means having one end thereof pivotably connected to said means defining said vertical axis so as to be pivotable about said vertical axis within a horizontal plane;

a second swivel plate means having one end thereof pivotably connected to a second end of said first swivel plate means so as to be pivotable within a horizontal plane about a second vertical axis laterally spaced from said vertical axis;

third swivel plate means pivotably connected to a second end of said second swivel plate means, and supporting said optical equipment, so as to be pivotable within a horizontal plane about a third vertical axis which is laterally spaced from said vertical and second vertical axes; and means pivotably mounting said optical equipment upon said third swivel plate means so as to be capable of disposing said optical equipment in vertical, inclined, and horizontally oriented modes about a horizontal axis, whereby as a result of the pivotably adjustable disposition of said first, second, and third swivel plate means about said vertical, second vertical, and third vertical axes, said optical equipment may always be able to be focused upon said vertical axis when disposed in either one of said vertical, inclined, or horizontally oriented modes.

3. A stand mechanism for supporting medical optical equipment, comprising:

parallel linkage means having a swivel member mounted upon an extremity thereof for supporting said optical equipment;

rotary shaft means, rotatable about a longitudinal axis thereof and having one end thereof connected to a second extremity end of said parallel linkage means such that said parallel linkage means extends substantially radially outwardly from said longitudinal axis of said rotary shaft means in a first direction with respect to said longitudinal axis of said rotary shaft means, for supporting said parallel linkage means and said optical equipment;

counterweight means, comprising first and second counterweights, movably mounted upon an opposite end of said rotary shaft means and extending substantially radially outwardly from said longitudinal axis of said rotary shaft means in a second direction opposite to said first direction of said parallel linkage means with respect to said longitudinal axis of said rotary shaft means, for counterbalancing the weight of said optical equipment and said parallel linkage means, and the moments created thereby, with respect to said longitudinal axis of said rotary shaft means when said parallel linkage means is transformed substantially within a plane which includes said parallel linkage means and said longitudinal axis of said rotary shaft means as a result of positional movement of said optical equipment, and when said optical equipment and said parallel linkage means are pivotably moved about said longitudinal axis of said rotary shaft means; and means for interconnecting said swivel member and said second counterweight so that movement of said optical equipment and said swivel member within a horizontal plane and with respect to said longitudinal axis of said rotary shaft means, and said moments created thereby, are counterbalanced by said second counterweight independent of said first counterweight.

4. A stand mechanism as set forth in claim 3, further comprising:

means defined upon said one extremity end of said parallel linkage means supporting said optical equipment for defining a vertical axis about which said optical equipment can be pivotably adjusted within a horizontal plane and upon which said optical equipment can be focused;

said swivel member having one end thereof pivotably connected to said means defining said vertical axis so as to be pivotable about said vertical axis within a horizontal plane;

first swivel plate means having one end thereof pivotably connected to a second end of said swivel member so as to be pivotable within a horizontal plane about a second vertical axis laterally spaced from said vertical axis;

second swivel plate means pivotably connected to a second end of said first swivel plate means, and supporting said optical equipment, so as to be pivotable within a horizontal plane about a third vertical axis which is laterally spaced from said vertical and second vertical axes; and means pivotably mounting said optical equipment upon said second swivel plate means, and about a horizontal axis, so as to be capable of disposing said optical equipment in vertical, inclined, and horizontally oriented modes with respect to said vertical axis, whereby as a result of the pivotably adjustable disposition of said swivel member and said first and second swivel plate means about said vertical, second vertical, and third vertical axes, said optical equipment may always be able to be focused upon said vertical axis when disposed in either one of said vertical, inclined, or horizontally oriented modes.

5. A stand mechanism as set forth in claim 3, wherein: said first and second counterweights comprise pendulous counterweights pivotably movable within a vertical plane.

6. A stand mechanism as set forth in claim 5, wherein: said means interconnecting said swivel member and said second counterweight includes means for permitting said second counterweight to be pivotably movable within a horizontal plane in response to said movement of said optical equipment and said swivel member within said horizontal plane.

7. A stand mechanism as set forth in claim 6, wherein said means for permitting said second counterweight to be pivotably movable within a horizontal plane comprises:

a plurality of bevel gears, rotary disks, and link bars interconnecting said bevel gears and said rotary disks.

8. A stand mechanism for supporting medical optical equipment, comprising:

first parallel linkage means for supporting said optical equipment upon one extremity end thereof;

multiple parallel linkage means connected to a second extremity end of said first parallel linkage means for providing vertically adjustable movement for said first parallel linkage means and said optical equipment supporting thereon, said multiple parallel linkage means comprising a second parallel linkage means having one end thereof operatively connected to said first parallel linkage means, a third parallel linkage means disposed beneath said second parallel linkage means, and linkage means interconnecting a second end portion of said second parallel linkage means to a first end portion of said third parallel linkage means; and counterweight means mounted upon a second end of said third parallel linkage means for counterbalancing the weight and moments of said first parallel linkage means and said optical equipment supported thereon as said first parallel linkage means and said optical equipment supported thereon is vertically adjusted.

9. A stand mechanism as set forth in claim 8, further comprising:

means defined upon said one extremity end of said parallel linkage means supporting said optical equipment for defining a first vertical axis about which said optical equipment can be pivotably adjusted within a horizontal plane and upon which said optical equipment can be focused;

first swivel plate means having one end thereof pivotably connected to said means defining said first vertical axis so as to be pivotable about said first vertical axis within a horizontal plane;

second swivel plate means having one end thereof pivotably connected to a second end of said first swivel plate means so as to be pivotable within a horizontal plane about a second vertical axis laterally spaced from said first vertical axis;

third swivel plate means pivotably connected to a second end of said second swivel plate means, and supporting said optical equipment, so as to be pivotable within a horizontal plane about a third vertical axis which is laterally spaced from said first and second vertical axes; and means pivotably mounting said optical equipment upon said third swivel plate means about a horizontal axis so as to be capable of disposing said optical equipment in vertical, inclined, and horizontal modes with respect to said first vertical axis, whereby as a result of the pivotably adjustable disposition of said first, second, and third swivel plate means about said first, second, and third vertical axes, said optical equipment may always be able to be focused upon said first vertical axis when disposed in either one of said vertical, inclined, or horizontal modes.

10. A stand mechanism for supporting medical optical equipment, comprising:

parallel linkage means having a swivel member mounted upon an extremity thereof for supporting said optical equipment;

rotary shaft means, rotatable about a longitudinal axis thereof and having one end thereof connected to a second extremity end of said parallel linkage means such that said parallel linkage means extends substantially radially outwardly from said longitudinal axis of said rotary shaft means in a first direction with respect to said longitudinal axis of said rotary shaft means, for supporting said parallel linkage means and said optical equipment;

counterweight means, comprising first and second counterweights, movably mounted upon an opposite end of said rotary shaft means and extending substantially radially outwardly from said longitudinal axis of said rotary shaft means in a second direction opposite to said first direction of said parallel linkage means with respect to said longitudinal axis of said rotary shaft means, for counterbalancing the weight of said optical equipment and said parallel linkage means, and the moments created thereby, with respect to said longitudinal axis of said rotary shaft means when said parallel linkage means is transformed substantially within a plane which includes said parallel linkage means and said longitudinal axis of said rotary shaft means as a result of positional movement of said optical equipment, and when said optical equipment and said parallel linkage means are pivotably moved about said longitudinal axis of said rotary shaft means;

means for interconnecting said swivel member and said second counterweight so that movement of said optical equipment and said swivel member within a horizontal plane and with respect to said longitudinal axis of said rotary shaft means, and said moments created thereby, are counterbalanced by said second counterweight independent of said first counterweight;

multiple parallel linkage means connected to said rotary shaft means for providing vertically adjustable movement of said rotary shaft means, said parallel linkage means, and said optical equipment; and third counterweight means mounted upon an end of said multiple parallel linkage means which isoppposite the end of said multiple parallel linkage means to which said rotary shaft means is connected so as to counterbalance the weight and moments of said parallel linkage means, said rotary shaft means, and said optical equipment.

11. A stand mechanism as set forth in claim 10, further comprising:

means defined upon said one extremity end of said parallel linkage means supporting said optical equipment for defining a first vertical axis about which said optical equipment can be pivtably adjusted within a horizontal plane and upon which said optical equipment can be focused;

said swivel member having one end thereof pivotably connected to said means defining said first vertical axis so as to be pivotable about said first vertical axis within a horizontal plane;

first swivel plate means having one end thereof pivotably connected to a second end of said swivel member so as to be pivotable within a horizontal plane about a second vertical axis laterally spaced from said first vertical axis;

second swivel plate means pivotably connected to a second end of said first swivel plate means, and supporting said optical equipment, so as to be pivotable within a horizontal plane about a third vertical axis which is laterally spaced from said first and second vertical axes; and means pivotably mounting said optical equipment upon said second swivel plate means about a horizontal axis so as to be capable of disposing said optical equipment in vertical, inclined, and horizontal modes with respect to said first vertical axis, whereby as a result of the pivotably adjustable disposition of said swivel member and said first and second swivel plate means about said first, second, and third vertical axes, said optical equipment may also be able to be focused upon said first vertical axis when disposed in either one of said vertical, inclined, and horizontal modes.

12. A stand mechanism as set forth in claim 10, wherein:

said first and second counterweights comprise pendulous counterweights pivotably movable within a vertical plane.

13. A stand mechanism as set forth in claim 12, wherein:

said means interconnecting said swivel member and said second counterweight includes means for permitting said second counterweight to be pivotably movable within a horizontal plane in response to said movement of said optical equipment and said swivel member within said horizontal plane.

14. A stand mechanism as set forth in claim 13, wherein said means for permitting sid second counterweight to be pivotably movable within a horizontal plane comprises:

a plurality of bevel gears, rotary disks, and link bars interconnecting said bevel gears and said rotary disks.

* * * * *